United States Patent
Miura et al.

(10) Patent No.: US 7,465,556 B2
(45) Date of Patent: Dec. 16, 2008

(54) METHOD OF IMMUNOASSAY TARTRATE RESISTANT ACID PHOSPHATASE 5B AND KIT TO BE USED THEREIN

(75) Inventors: Toshihide Miura, Koriyama (JP); Tatsuya Ohashi, Koriyama (JP); Kumiko Sasagawa, Koriyama (JP); Katsuhiro Katayama, Koriyama (JP)

(73) Assignee: Nitto Boseki Co., Ltd., Fukushima-Shi (JP)

( * ) Notice: Subject to any disclaimer, the term of this patent is extended or adjusted under 35 U.S.C. 154(b) by 0 days.

(21) Appl. No.: 10/546,608

(22) PCT Filed: Feb. 20, 2004

(86) PCT No.: PCT/JP2004/001957

§ 371 (c)(1),
(2), (4) Date: Aug. 23, 2005

(87) PCT Pub. No.: WO2004/077059

PCT Pub. Date: Sep. 10, 2004

(65) Prior Publication Data

US 2006/0154317 A1    Jul. 13, 2006

(30) Foreign Application Priority Data

Feb. 25, 2003   (JP)   ............................. 2003-046750

(51) Int. Cl.
*C12Q 1/42* (2006.01)
*G01N 33/573* (2006.01)
*G01N 33/53* (2006.01)
*G01N 33/535* (2006.01)

(52) U.S. Cl. ..................... 435/21; 435/7.1; 435/7.4; 435/7.9; 435/7.92; 435/7.94; 436/815

(58) Field of Classification Search ................ 435/7.1, 435/7.4, 7.9, 7.92, 7.94, 21, 7; 436/815
See application file for complete search history.

(56) References Cited

U.S. PATENT DOCUMENTS

| | | | | |
|---|---|---|---|---|
| 4,983,512 A | * | 1/1991 | Teshima et al. | ............... 435/21 |
| 6,248,544 B1 | | 6/2001 | Halleen et al. | ............... 435/7.4 |
| 6,448,027 B1 | | 9/2002 | Nakanishi et al. | ............. 435/21 |

2003/0204062 A1   10/2003   Ohashi et al.   ........... 530/388.26

FOREIGN PATENT DOCUMENTS

| | | |
|---|---|---|
| JP | 10-337198 | 12/1998 |
| JP | 2001-231595 | 8/2001 |
| JP | 2004-26805 | 1/2004 |
| WO | WO99/50662 | 10/1999 |

OTHER PUBLICATIONS

Nakanishi et al; "Development of a Kinetic Assay for Band 5b Tartrate-resistant Acid Phosphatase Activity in Serum;" Clinical Chemistry 46:4 (2000) pp. 469-473.
Chamberlain et al; "Generation and Characterization of Monoclonal Antibodies to Human Type-5 Tartrate-Resistant Acid Phosphatase: Development of a Specific Immunoassay of the Isoenzyme in Serum;" Clin. Chem. 41/10 (1995) pp. 1495-1499.
European Supplementary Report dated May 8, 2006.
Alatalo et al; "Rapid Screening Method of Osteoclast Differentiation in Vitro that Measures Tartrate-resistant Acid Phosphatase 5b Activity Secreted in the Culture Medium;" Clinical Chemistry 46:11 (2000); pp. 1751-1754.
Nakasato et al; "Clinical Significance of Immunoassays for Type-5 Tartrate-resistant Acid Phosphatase;" Clinical Chemistry 45:12 (1999); pp. 2150-2157.
Halleen et al; "Two-site Immunoassays for Osteoclastic Tartrate-Resistant Acid Phosphatase Based on Characterization of Six Monoclonal Antibodies;" J. Bone Mineral Research, vol. 14, No. 3 (1999); pp. 464-469.
Bull et al; "Reactivity and assay restriction profiles of monoclonal and polyclonal antibodies to acid phosphatases: a preliminary study;" Immunology Letters 70 (1999) pp. 143-149.
Halleen et al; "Characterization of Serum Tartrate-Resistant Acid Phosphatase and Development of a Direct Two-site Immunoassay;" J. Bone Mineral Research, vol. 13, No. 4 (1998); pp. 683-687.
Kraenzlin et al; "Development of an Immunoassay for Human Serum Osteoclastic Tartrate-Resistant Acid Phosphatase;" J. Clinical Endocrinology Metabolism; vol. 71, No. 2 (1990); pp. 442-451.

(Continued)

*Primary Examiner*—Long V Le
*Assistant Examiner*—Shafiqul Haq
(74) *Attorney, Agent, or Firm*—Kratz, Quintos & Hanson, LLP

(57) ABSTRACT

Specific and accurate immunoassay of tartrate resistant acid phosphatase 5b (TRACP 5b) in a specimen may be carried out by bonding TRACP 5b in the specimen to an antibody, subjecting the TRACP 5b bonded to the antibody to enzyme reaction with a 2-halo-4-nitrophenylphosphoric acid or a salt thereof, a substrate for TRACP 5b, and then assaying the enzymatic activity of TRACP 5b.

4 Claims, 1 Drawing Sheet

OTHER PUBLICATIONS

Lau et al; "Characterization and Assay of Tartrate-Resistant Acid Phosphatase Activity in Serum: Potential Use to Assess Bone Resorption;" Clin. Chem. 33/4 (1987); pp. 458-462.

"Standardization of Bone Marker Nomenclature;" Clinical Chemistry 47, No. 8 (2001), p. 1497. (see specification).

Onishi; "Study of Human Serum Tartrate-Resistant Acid Phopshatase;" J. Nihon Univ. Med. Assn., 49(9): pp. 904-911 (1990).

Fukunaga et al; "Osseous Metabolism Marker;" Medical Review Co., Ltd. (1995) pp. 74-83 (see specification).

Haleen, et al.; "Tartrate-resistant acid phosphatase 5b: a novel serum marker of bone resportion;" *J. Bone Miner Res.*; vol. 15; No. 7; 2000; pp. 1337-1345.

H. Bull et al.; "*Acid Phosphatases*"; J Clin Pathol: Mol Pathol, 2002; 55:65-72.

* cited by examiner

METHOD OF IMMUNOASSAY TARTRATE RESISTANT ACID PHOSPHATASE 5B AND KIT TO BE USED THEREIN

TECHNICAL FIELD

The present invention relates to a method for immunoassay of tartrate resistant acid phosphatase activity derived from osteoclast as a bone resorption marker and a kit to be used therein. According to the present invention, specific assay of tartrate resistant acid phosphatase activity derived from osteoclast is possible and this activity is very effective as a bone resorption marker in the fields of medical treatments and clinical examinations of bone diseases.

BACKGROUND ART

A large portion of tartrate resistant acid phosphatase (TRACP) in serum is considered acid phosphatase derived from osteoclast and the assay of TRACP is considered useful as an indication for evaluating the function of osteoclast. Thus, TRACP is gaining interest as a bone resorption marker (Norio Fukunaga, Toshitaka Nakamura and Toshio Matsumoto, "Osseous Metabolism Marker", Medical Review Co., Ltd., 1995). On the other hand, acid phosphatase in serum is divided into six bands 0 to 5 from the origin by polyacrylamide gel electrophoresis. Of these, acid phosphatase corresponding to the fifth band is tartrate-resistant and is called Band 5 tartrate resistant acid phosphatase (TRACP 5: tartrate resistant acid phosphatase 5). This acid phosphatase is further divided by electrophoresis into 5a which has a high content of sialic acid bonded to a sugar chain and 5b which has almost no sialic acid bonded to a sugar chain. In addition, 5a is an enzyme derived from cells other than osteoclast and its blood level does not vary, while only the blood level of 5b varies with bone resorption. Therefore, it is considered that 5b is the main substance of tartrate resistant acid phosphatase derived from osteoclast. Also in "Clinical Chemistry" (Clin. Chem. 47: 1497. 2001), it is recommended that ACP derived from osteoclast should be abbreviated as TRACP 5b. Accordingly, also in the present specification, phosphatase that refers to ACP derived from osteoclast and used as an indication of bone resorption is expressed in the term "TRACP 5b", and tartrate resistant acid phosphatase derived from osteoclast and tartrate resistant acid phosphatase 5b are hereinafter considered synonymous with each other. Thus, all of them are hereinafter expressed in the term "TRACP 5b" in the present specification.

Conventional activity assay methods in which TRACP activity is assayed as an indication of acid phosphatase capable of indicating the activity of osteoclast are disadvantageous in specificity, sensitivity, troublesomeness of assay and assay time.

In general, in the assay of TRACP 5b by the activity assay method, the enzymatic activity is assayed by colorimetric determination of a reaction product (an alcohol or a phenol) produced by an enzyme reaction, by using a phosphoric ester as a synthetic substrate in the presence of tartaric acid. In this case, tartaric acid inhibits acid phosphatase derived from prostate and the residual acid phosphatase activity is assayed with the substrate to assay TRACP activity as TRACP 5b activity. However, besides tartrate resistant acid phosphatase derived from osteoclast, that derived from erythrocyte or that derived from platelet is present in a specimen, and such acid phosphatase is also assayed. Therefore, the above TRACP 5b assay method is disadvantageous in specificity.

As a modification of such a method, there is known a method in which after a pretreatment comprising incubation of a 5-fold dilution of serum at 37° C. for 1 hour, the residual TRACP activity is assayed by the use of p-nitrophenylphosphoric acid as a substrate in the presence of tartaric acid ("Nichidai-Ishi", 49:904-911. 1990; and Clin. Chem. 33:458-462. 1987). This method permits avoidance of the influence of acid phosphatase derived from erythrocyte but does not permit exclusion of the influence of acid phosphatase derived from platelet. In addition, the present inventors have reported a TRACP 5b assay method utilizing the difference in sensitivity to fluorine between TRACP 5b and tartrate resistant acid phosphatase activity derived from erythrocyte or platelet, as a more specific activity assay method (JP-A-10-37198). This method, however, does not permit exclusion of the influence of TRACP 5a though it permits avoidance of the influence of tartrate resistant acid phosphatase derived from erythrocyte or platelet. Moreover, this method is disadvantageous in precision because TRACP 5b activity is assayed in this method by subtracting activity not inhibited in the presence of fluorine from the total tartrate resistant acid phosphatase activity. In addition, a method has been reported in which TRACP 5b activity is assayed by using an inhibitor for TRACP 5a in combination with the above-mentioned method utilizing fluorine (JP-A-2001-231595). However, since TRACP 5b activity is assayed by the subtraction also in this method, this method is disadvantageous in precision like the method using only fluorine, though it is more specific than the latter method.

On the other hand, as TRACP 5b assay methods using immunoassay, there are also known immunoassay methods using a polyclonal antibody or a monoclonal antibody (J Clin Endocrinol Metab. 71:442-451. 1990; J Bone Miner Res. 13:683-687. 1998; Immunol Lett. 70:143-149. 1999; J Bone Miner Res. 14:464-469. 1999; Clin Chem. 45:2150-2157. 1999; and Clin Chem. 46:1751-1754. 2000). In these methods, activity corresponding to the whole of Band 5 is assayed, so that the influence of TRACP 5a is not negligible. In addition, an immunoassay method has been reported in which TRACP 5b is more specifically assayed (Japanese Patent Application Kohyo No. 2002-510050). It has been reported that this method is an assay method more specific for TRACP 5b activity because in this method, measured values are obtained by activity assay by utilizing the difference in optimum pH between TRACP 5a and TRACP 5b. However, since the antibody used in this method is not specific for TRACP 5b, this method is not always sufficient in specificity for TRACP 5b and hence is desired to be further improved in order to use TRACP 5b as a bone resorption marker.

DISCLOSURE OF THE INVENTION

In view of such problems, the present invention is intended to provide a method for assaying TRACP 5b as a bone resorption marker specifically with high sensitivity, and a kit to be used in this method.

The present invention provides a method for immunoassay of tartrate resistant acid phosphatase 5b (TRACP 5b) in a specimen which comprises bonding TRACP 5b in the specimen to an antibody, subjecting the TRACP 5b bonded to the antibody to enzyme reaction with a 2-halo-4-nitrophenylphosphoric acid represented by the general formula (1):

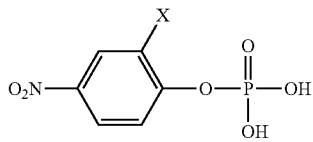

wherein X is Cl, F, Br or I, or a salt thereof, which is a substrate for TRACP 5b, and then assaying the enzymatic activity of TRACP 5b to carry out the immunoassay of TRACP 5b in the specimen.

The present invention also provides a kit for immunoassay of TRACP 5b which comprises
  i) a solid support,
  ii) an antibody against TRACP 5b, and
  iii) a substrate for TRACP 5b which is a 2-halo-4-nitrophenylphosphoric acid represented by the general formula (1):

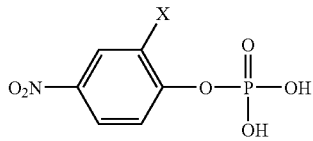

wherein X is Cl, F, Br or I, or a salt thereof.

MODE FOR CARRYING OUT THE INVENTION

Figure 1:
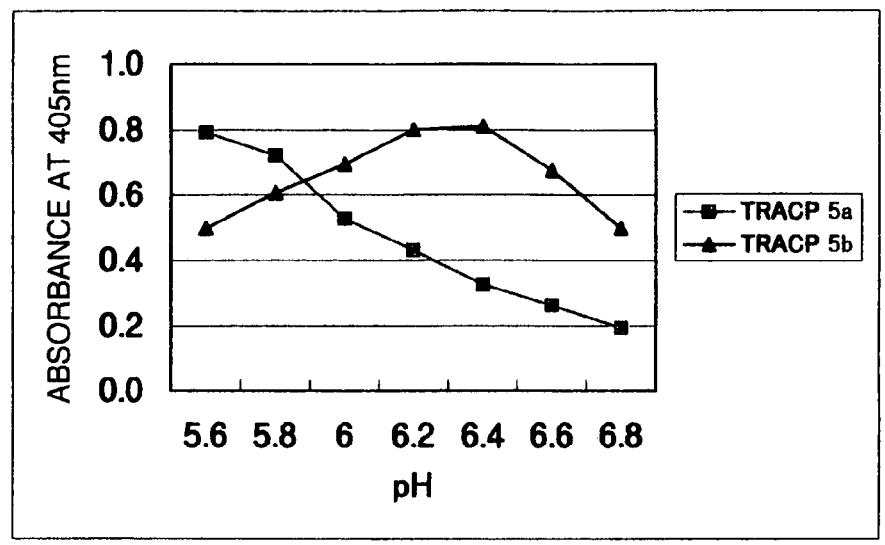
FIG. 1 is a graph showing the optimum pH in the assay of the enzymatic activity of each of TRACP 5b and TRACP 5a by the use of 2-chloro-4-nitrophenylphosphoric acid (CNPP) as a substrate for enzyme.

The specimen to be subjected to assay in the present invention includes human blood, serum, plasma and the like and is not particularly limited so long as it is likely to contain TRACP 5b.

In the present invention, the antibody is preferably bonded to a solid support. In addition, as the antibody, either a monoclonal antibody or a polyclonal antibody may be used so long as they are antibodies against TRACP 5b, though the monoclonal antibody is preferable from the viewpoint of specificity. As the monoclonal antibody, heretofore-known monoclonal antibodies against TRACP 5b may be used.

As the antibody used in the present invention, a monoclonal antibody against TRACP 5b may be prepared by using TRACP 5b purified from human osteoclast, as an immunogen. The monoclonal antibody is produced, for example, by hybridoma obtained by immunizing an animal with purified human TRACP 5b as an immunogen and fusing cells capable of producing anti-human TRACP 5b antibody, which are produced by the animal, with myeloma cells.

The above-mentioned hybridoma may be obtained by the following method. That is, human TRACP 5b is mixed with a well-known adjuvant such as Freund's complete or incomplete adjuvant, aluminum hydroxide adjuvant, pertussis adjuvant or the like to prepare an adjuvant liquid for sensitization, and this liquid is administered to an animal (e.g. a mouse or a rat) subcutaneously in the abdominal cavity or intravenously in the tail, in several portions at intervals of 1 to 3 weeks to immunize the animal. Although the amount of the antigen used for the sensitization is usually chosen in the range of 1 μg to 100 mg, it is preferably about 50 μg in general. Although the number of immunizing operations is generally 2 to 7, various methods are known. Subsequently, antibody-producing cells derived from the spleen or the like are fused with cells having proliferating capability in a test tube, such as myeloma cells or the like. The antibody-producing cells may be obtained from the spleen or the like of a mouse, a nude mouse, a rat or the like.

As to a method for the fusion, the fusion may be carried out by the use of a poly(ethylene glycol) (PEG) by the method of Köhller and Milstein (Nature. 256, 495. 1975) which is already per se well known. The fusion may be carried out also by the use of Sendai virus or by an electrofusion method.

As to a method for selecting hybridoma capable of producing an antibody capable of recognizing human TRACP 5b, from the fused cells, the selection may be carried out as follows. That is, the hybridoma is selected from colonies formed by cells surviving in HAT medium and HT medium in limiting dilution of the fused cells. When an antibody against human TRACP 5b is contained in the supernatant of the culture medium for any of the colonies formed by the fused cells seeded into a 96-well plate or the like, a clone capable of producing a monoclonal antibody against human TRACP 5b may be selected by an ELISA method in which the supernatant is placed on an assay plate having human TRACP 5b immobilized thereon, and after the reaction, a secondary labeled antibody such as an anti-mouse immunoglobulin-HRP labeled antibody is reacted with the above-mentioned antibody. As the labeling substance of the labeled antibody, there may be used enzymes (e.g. alkaline phosphatase), fluorescent substances, radioactive substances and the like besides HRP. Screening of specific antibodies against human TRACP 5b may be conducted by carrying out, as a control, ELISA using an assay plate having only BSA bonded thereto as a blocking agent, simultaneously with the above-mentioned ELISA. That is, a clone may be selected which is positive on the plate having human TRACP 5b immobilized thereon and is negative in the ELISA using only BSA.

As the thus selected hybridomas capable of producing a monoclonal antibody against TRACP 5b, hybridomas TrK27, TrK49 and TrK62 may be exemplified. Hybridomas TrK27, TrK49 and TrK62 were deposited as follows in Patented Organism Deposition Center (IPOD), Industrial Technology General Research Institute (Independent Administrative Corporation), Chuo-dairoku, Higashi 1-1-1, Tsukuba City, Ibaraki Prefecture, Japan 305-8566: hybridoma TrK27 was deposited as a receipt number IPOD FERMBP-7889 on Feb. 14, 2002, hybridoma TrK49 was deposited as a receipt number IPOD FERM BP-8249 on Nov. 27, 2002, and hybridoma TrK62 was deposited as a receipt number IPOD FERMBP-7890 on Feb. 14, 2002.

Each of the hybridomas is cultured on a medium usually used for cell culture, such as α-MEM, RPMI1640, ASF, S-clone or the like, and the monoclonal antibody may be recovered from the supernatant of the culture medium. The following is also possible: after an animal from which the hybridoma has been derived, such as a mouse is previously treated with pristine, the hybridoma is intraperitoneally injected into the animal to cause accumulation of ascites, and the monoclonal antibody is recovered from the ascites. As a method for recovering the monoclonal antibody from the supernatant or the ascites, a conventional method may be adopted. There are exemplified salting-out with ammonium sulfate, sodium sulfate of the like, chromatography, ion exchange chromatography, and affinity chromatography using protein A, protein G or the like.

As the monoclonal antibody used in the present invention, a monoclonal antibody reactive with not only TRACP 5b but also TRACP 5a may be used. In the present invention, a polyclonal antibody may be used. The polyclonal antibody may be obtained, for example, by using TRACP 5b purified from human osteoclast, as an immunogen, immunizing an animal such as a rat or mouse with this TRACP 5b, and preparing antiserum from the animal.

In the present invention, the immunoassay of TRACP 5b in a specimen is carried out by bonding TRACP 5b in the specimen to the above-mentioned antibody, subjecting the bonded TRACP 5b to enzyme reaction with a 2-halo-4-nitrophenylphosphoric acid of the general formula (1) or a salt thereof, as a substrate for enzyme, and then assaying the enzymatic activity.

As the 2-halo-4-nitrophenylphosphoric acid used in the present invention, there may be exemplified 2-chloro-4-nitrophenylphosphoric acid, 2-fluoro-4-nitrophenylphosphoric acid and 2-bromo-4-nitrophenylphosphoric acid. As the salt of the 2-halo-4-nitrophenylphosphoric acid, there may be exemplified its ammonium salt, imidazolium salt, cyclohexylammonium salt, potassium salt, sodium salt and tris(hydroxyammonium) salt.

The above-mentioned substrate used in the present invention has a lower Km value for TRACP 5b and a higher Km value for TRACP 5a than does p-nitrophenylphosphoric acid (PNPP), and hence is very advantageous in sensitivity and specificity when used for assaying TRACP 5b.

In the present invention, when TRACP 5b in a specimen is subjected to enzyme reaction with the 2-halo-4-nitrophenylphosphoric acid or its salt, a substrate for TRACP 5b, the pH at the reaction is preferably higher than 6.3 and not higher than 6.8, more preferably 6.35 to 6.75, in particular, 6.38 to 6.70. When the pH is too low, the enzyme reaction of TRACP 5a becomes liable to occur, resulting in a low ratio of TRACP 5b reactivity to TRACP 5a reactivity. Therefore, the specificity for TRACP 5b tends to be insufficient. When the pH is too high, the enzyme reaction of TRACP 5b itself does not occur easily, so that the measurement sensitivity tends to be lowered.

In the present invention, specifically, TRACP 5b may be assayed as follows by adopting, for example, an end-point method. At first, a specimen to be subjected to assay is added to an antibody adsorbed on a solid support to subject TRACP 5b in the specimen and the antibody to antigen-antibody reaction and bond TRACP 5b to the antibody. Then, the solid support is washed with a washing solution to remove components contained in the specimen and not adsorbed on the antibody. Thereafter, the 2-halo-4-nitrophenylphosphoric acid or its salt is added to the reaction system as a substrate for enzyme to react the substrate with the TRACP 5b bonded to the antibody, preferably at a pH of higher than 6.3 and not higher than 6.8. After the enzyme reaction is terminated with a reaction-terminating solution, the 2-halo-4-nitrophenol produced by the reaction is subjected to absorbance measurement at a wavelength of 390 nm to 450 nm, preferably 400 to 430 nm. Since the value of the absorbance reflects the enzymatic activity of TRACP 5b, TRACP 5b in the specimen may be assayed on the basis of the absorbance value.

In the present invention, rate assay may also be carried out as the assay of the enzymatic activity unlike in a conventional method using p-nitrophenylphosphoric acid because the 2-halo-4-nitrophenol develops a color at the pH at the reaction. When the rate assay is carried out, TRACP 5b in a specimen may be assayed by measuring the reactivity of TRACP 5b with the substrate as an average absorbance change per a definite time (usually 1 minute). As a result, the measurement time is reduced, which is more desirable.

In the present invention, as is clear from the assay method described above, the antibody is preferably used after being bonded to a solid support. The solid support is not particularly limited though a solid support used in a solid phase immunoassay method such as ELISA is usually used. A material for solid support includes, for example, polystyrenes, polypropylenes, polycarbonates, polyethylenes, nylons and methacrylates. As the shape of the solid support, a plate shape and a bead shape are exemplified.

For preparing the antibody adsorbed on the solid support, the antibody against TRACP 5b is directly or indirectly bonded to the solid support by utilizing physical bonding, chemical bonding or affinity. The amount of the antibody used for the sensitization is often in the range of 1 ng to 100 mg/ml.

The method of the present invention may be practiced by the use of a kit for immunoassay of TRACP 5b which comprises i) a solid support, ii) an antibody against TRACP 5b, and iii) a substrate that is a 2-halo-4-nitrophenylphosphoric acid of the general formula (1) or a salt thereof.

In this kit, as to i) the solid support and ii) the antibody against TRACP 5b, it is possible to prepare the solid support and a solution of the antibody separately and adsorb the antibody on the solid support at the time of assay of TRACP 5b. Alternatively, the kit may be provided after the previous adsorption of the antibody on the solid support. The kit preferably comprises a washing solution for the purpose of removing components not adsorbed on the solid support, after the bonding of TRACP 5b in a specimen to the antibody. For example, Tris buffer containing a surfactant may be used as the washing solution.

When this kit is used in an end-point method, the kit preferably comprises an enzyme-reaction-terminating solution. As the enzyme-reaction-terminating solution, there may be used, for example, aqueous alkali solutions such as solutions of potassium hydroxide, sodium hydroxide and the like.

In addition, the kit of the present invention may further comprises a diluent for specimen if necessary. For example, a buffer solution such as Tris buffer may be used as the diluent for specimen. If necessary, a chelating agent (e.g. EDTA.2Na) and an inorganic salt (e.g. sodium chloride) may be added to the buffer solution.

The present invention is illustrated in further detail with reference to the following reference examples and working examples, which should not be construed as limiting the scope of the invention.

REFERENCE EXAMPLE 1

Preparation of a Monoclonal Antibody Against TRACP 5b (1) Purification of Acid Phosphatase TRACP 5b Derived from Osteoclast After informed consent was obtained, 130 g of the caput of human thigh bone excised by a surgical operation was frozen in liquid nitrogen, crushed with a hammer, and then suspended in 200 mL of a buffer solution (50 mM Tris-HCl, 0.3M KCl, 1 mM PMSF, 1 mM EDTA.2Na, 0.1% Triton X-100, 0.02% $NaN_3$, 1 unit/ml aprotinin, pH 7.5) containing a protease inhibitor, followed by homogenization in a ultrasonic homogenizer. The homogenate was stirred overnight at 4° C. and centrifuged at 10,000 rpm for 20 minutes, and the supernatant was dialyzed against 10 mM Tris buffer (pH 8.2). Thereafter, the dialyzed solution was applied to a CM-Sepharose column (Φ40 mm×40 cm) [Sigma Chemical Co.] and the protein adsorbed was eluted with the same Tris buffer as above containing NaCl, while increasing the NaCl concentration with a linear concentration gradient (0-0.5M NaCl). Tartrate resistant acid phosphatase activity was assayed with a substrate 2,6-dichloro-4-acetylphenylphosphoric acid [mfd. by Nitto Boseki Co., Ltd.], and fractions containing a high level of the activity were pooled. The solution thus obtained was concentrated and then dialyzed against 20 mM Tris buffer (pH 7.2) containing 0.7 M NaCl, and the dialyzed solution was applied to a Superdex 200 column (Φ16 mm×60 cm) [Amersham Pharmacia Biotech AB]. In the same manner as above, tartrate resistant acid phosphatase activity in fractions obtained by elution was assayed and fractions containing the activity were pooled. The solution thus obtained was diluted 2-fold with 20 mM Tris buffer (pH 7.2) and applied to a HiTrap Heparin HP column (5 mL) [Amersham Pharmacia Biotech AB], and the protein adsorbed was eluted with the same 20 mM Tris buffer (pH 7.4) as above containing NaCl, while increasing the NaCl concentration with a linear concentration gradient (0.35-1M NaCl). Fractions containing a high tartrate resistant acid phosphatase activity were pooled and then concentrated to obtain 0.4 mg of purified acid phosphatase derived from osteoclast. The amount of the protein was confirmed by $A_{280}$. As to the purity, SDS-PAGE [TIFCO] was carried out, followed by silver staining. As a result, the purity was confirmed by the appearance of a single band at a molecular weight of about 35,000. The enzyme corresponding to the single band was considered as purified TRACP 5b and was used as an immunizing antigen.

(2) Immunization

The purified tartrate resistant acid phosphatase derived from human osteoclast (TRACP 5b) was diluted to a concentration of 250 μg/ml with 50 mM citrate buffer (pH 5.5), and 25 μg (100 μl) of the dilution was thoroughly mixed with 100 μl of Freund's complete adjuvant [Wako Pure Chemical Industries, Ltd.] until emulsification was effected. The suspension thus prepared was intraperitoneally administered to a Balb/c female mouse aged 6 weeks [Nippon Clear Co., Ltd.] under anesthesia with diethyl ether. After 2 weeks, the same amount as above of TRACP 5b (25 μg/ml) was mixed with Freund's incomplete adjuvant [Wako Pure Chemical Industries, Ltd.]. By exactly the same operation as in the case of the Freund's complete adjuvant, emulsification was effected to obtain a suspension and the mouse was sensitized with the suspension. Two weeks after this procedure, the same procedure as above was carried out. For the fourth immunization, i.e., final immunization, a dilution of TRACP 5b (25 μg/ml) with 50 mM citrate buffer (pH 5.5) was prepared and then administered to the mouse by injection into the tail vein.

(3) Establishment of Hybridoma

Three days after the final immunization, the spleen was surgically removed from the mouse sensitized with TRACP 5b, under anesthesia with diethyl ether, and was aseptically dispersed to prepare splenocytes. Fusion was carried out according to the method of KÖhller and Milstein (Nature, 256, 495, 1975). The splenocytes were fused with myeloma cells P3-X63-Ag8-U1 (P3U1) by the use of a poly(ethylene glycol) (PEG4000) [Merck & Co., Inc.]. As to the fusion ratio, the number of the splenocytes was $8\times10^7$, while the number of the myeloma cells P3-X63-Ag8-U1 (P3U1) was $2\times10^7$. That is, the fusion ratio of the splenocytes to the myeloma cells was 4:1. The fused cells were dispersed in 10% FCS [INVITROGEN] α-MEM [IRVINE] HAT [Cosmo Bio Co., Ltd.] medium, seeded into a 96-wells microtiter culture plate [Sumitomo Bakelite Co., Ltd.] and then cultured under conditions of 37° C. and 5% $CO_2$.

(4) Screening

After about 2 weeks, the growth of colonies was confirmed and screening was conducted. A method for conducting the screening is described below. For producing a plate for the screening, TRACP 5b purified in the above item (1) was dissolved in 50 mM citrate buffer and applied to a 96-well plate [Nunc] in an amount of 0.5 μg/100 μl/well. The plate was allowed to stand at 4° C. for two nights and then washed three times with Tris buffer containing 0.05% Tween 20. To each well was applied 200 μl of 1.5% BSA solution in order to inhibit a nonspecific reaction, and the plate was allowed to stand overnight at 4° C. After the thus completed plate was washed three times with Tris buffer containing 0.05% Tween 20, 100 μl of the culture supernatant was reacted in each well and the plate was further washed. Then, HRP-labeled anti-mouse immunoglobulin antibody [Zymed Laboratories, Inc.], a secondary antibody was added to carry out the reaction. After washing, 100 μl of a 3 mg/ml color-producing solution of o-phenylenediamine (OPD) [Nacalai Tesque Inc.], a color-producing substrate for HRP, in citric acid was added to each well to cause coloration for a definite period. Then, 100 μl of 1N sulfuric acid was added to each well as a terminating solution and absorbance was measured at a measuring wavelength of 492 nm. Clones found to be positive by the above procedure were subjected to recloning by a limiting dilution method, and the supernatants thus obtained were checked again.

(5) Confirmation of an Antibody

The reaction of clone TrK27 with purified TRACP 5b was confirmed by ELISA and clone TrK27 was selected as a clone capable of producing an antibody reactive with TRACP 5b. This hybridoma TrK27 was deposited as a receipt number IPOD FERMBP-7889 on Feb. 14, 2002 in Patented Organism Deposition Center (IPOD), Industrial Technology General Research Institute (Independent Administrative Corporation), Chuo-dairoku, Higashi 1-1-1, Tsukuba City, Ibaraki Prefecture, Japan 305-8566.

An antibody produced by this hybridoma was assayed by the use of a monoclonal antibody typing kit [Amersham Pharmacia Biotech AB] to find that its class was IgG1 and that its light chain was κ. The specificity of this antibody was investigated as follows. ELISA was carried out by using, as a specimen, each of TRACP 5b, TRACP 5a derived from human serum and eluted from a HiTrap Heparin HP column, ACP derived from prostate, ACP derived from platelet (a platelet extract solution) and ACP derived from erythrocyte (an erythrocyte extract solution). As a result, the antibody reacted with TRACP 5b and TRACP 5a but not with the other isoforms.

(6) Preparation and Purification of a Monoclonal Antibody

To a Balb/c female mouse aged 10 weeks [Nippon Clear Co., Ltd.] two weeks after administration of 0.5 ml of pristane [Aldrich Chemical Co.] to the mouse were intraperitoneally administered $1\times10^7$ cells of the obtained hybridoma TrK27. After about 2 weeks, ascites accumulated in the abdominal cavity of the mouse was surgically collected under anesthesia with diethyl ether. As a result of confirmation by the use of the ascites stepwise diluted as a sample and by the ELISA method adopted for the screening, it was found that the ascites contained a high concentration of a monoclonal antibody. The ascites was treated with 40% ammonium sulfate and dialyzed against PBS, and then the monoclonal antibody was purified by the use of a protein G column [Amersham Pharmacia Biotech AB] and confirmed by SDS-PAGE. As a result, a single band was confirmed at a molecular weight of about 150,000 when the antibody was in a non-reduced state, and two bands were confirmed at molecular weights of about 50,000 and 25,000 when the antibody had been reduced with mercaptoethanol. The amount of the purified antibody was about 15 mg per mouse, namely, it was sufficient for industrial utilization.

(7) Production of a Plate having an Anti-TRACP 5b Antibody Immobilized Thereon

The antibody obtained in the above item (6) was dissolved in PBS and the resulting solution was applied to a 96-well plate [Nunc] in an amount of 1 µg/200 µl/well. The plate was allowed to stand at 4° C. for two nights and then washed three times with Tris buffer containing 0.05% Tween 20. To each well was applied 200 µl of 1.5% BSA solution in order to inhibit a nonspecific reaction, and the plate was allowed to stand overnight at 4° C. to complete a plate having an anti-TRACP 5b antibody immobilized thereon.

REFERENCE EXAMPLE 2

Comparison Between the Substrate Used in the Present Invention and Another Substrate by Km Measurement In order to investigate the difference between TRACP 5b and TRACP 5a in reactivity with 2-chloro-4-nitrophenylphosphoric acid (CNPP), Km for each of them was measured. As a result, it was found that Km was 1.5 mM (pH 6.4) for TRACP 5b and 3.5 mM (pH 5.6) for TRACP 5a. The Km value for TRACP 5b is less than one-half that for TRACP 5a, indicating that the substrate CNPP is more suitable for the assay of TRACP 5b than for that of TRACP 5a.

On the other hand, according to Clin. Chem., 47(1), 74-80, Km values in the reaction of each of TRACP 5b and TRACP 5a with p-nitrophenylphosphoric acid (PNPP) are 7.0 mM (pH 5.8) and 1.9 mM (pH 5.2), respectively. That is, for the assay of TRACP 5b, CNPP used in the present invention is more advantageous than PNPP from the viewpoint of affinity and specificity.

EXAMPLE 1

Assay of TRACP 5b or 5a at Various pH Values

The pH of a buffer solution containing a substrate CNPP was varied from 5.6 to 6.8 and the activity of TRACP 5b and TRACP 5a for this substrate was assayed. This substrate buffer solution had the following composition: CNPP 5 mM, Mes 0.1 M and sodium tartrate 40 mM. Its pH was adjusted to values varying from 5.6 to 6.8 by steps of 0.2. TRACP 5b and TRACP 5a used as samples were prepared by separating human serum by the use of a Heparin column and concentrating a fraction corresponding to a peak due to each of TRACP 5a and TRACP 5b. As TRACP 5a, there was used a sample having such a concentration that its absorbance was 0.8 at pH 5.6 (the optimum for TRACP 5a). As TRACP 5b, there was used a sample having such a concentration that its absorbance was 0.8 at pH 6.4 (the optimum for TRACP 5b). As to a method for the assay, a plate having an anti-TRACP 5b antibody Trk27 immobilized thereon was used and 100 µl of each sample was added to each well and stirred with shaking at room temperature for 1 hour. Then, the reaction solution was discarded and each well was washed three times with 200 µl of Tris buffer containing 0.05% Tween 20. Thereafter, 100 µl of the substrate buffer solution was added to each well and shaken for 30 seconds, followed by incubation in an incubator at 37° C. for 1 hour. Then, 50 µl of 0.2N NaOH was added to each well to terminate the enzyme reaction and the absorbance of the reaction solution was measured with a microtiter plate reader. The results are shown in FIG. 1. Under such conditions, the optimum pH for TRACP 5b was about 6.4 and that for TRACP 5a was 5.6.

EXAMPLE 2

Comparison Between the Present Invention and a Method Using PNPP (a Conventional Substrate)

Absorbance values due to the reaction of a buffer solution containing a substrate CNPP with each of TRACP 5a and TRACP 5b at pHs 6.2, 6.4, 6.6 and 6.8 were compared with results obtained in a comparative example using a buffer solution (pH 6.1) containing, as a substrate, PNPP that is considered suitable for the assay of TRACP 5b. According to the method disclosed in Japanese Patent Application Kohyo No. 2002-510050, the composition of this PNPP substrate buffer solution was as follows: PNPP 8 mM, sodium acetate 0.1M, sodium tartrate 40 mM, pH 6.1. As a sample of TRACP 5b, the same sample as in Example 1 was used. As a sample of TRACP 5a, a sample was used which had been prepared so that in the comparative example (PNPP was used at pH 6.1), a value for TRACP 5a might be one-tenth that for TRACP 5b according to the data disclosed in Japanese Patent Application Kohyo No. 2002-510050. The same assay procedure as in Example 1 was carried out and absorbance was used as an indication of the enzymatic activity. The results are shown in Table 1. As is clear from the results, the 5b/5a ratios at pHs 6.4 and 6.6 in the case of CNPP are 17 and 18, respectively, indicating that the method of the present invention is more suitable for assay of TRACP 5b than the conventional method (the comparative example).

TABLE 1

| Sample | Example 2 (CNPP) | | | | Comparative Example (PNPP) |
| --- | --- | --- | --- | --- | --- |
| | pH 6.2 | pH 6.4 | pH 6.6 | pH 6.9 | pH 6.1 |
| TRACP 5a | 0.062 | 0.047 | 0.038 | 0.025 | 0.098 |
| TRACP 5b | 0.802 | 0.811 | 0.674 | 0.401 | 0.981 |
| TRACP 5b/5a | 13 | 17 | 18 | 16 | 10 |

EXAMPLE 3

Method for Assaying TRACP 5b Activity by a Rate Method

Figure 2:
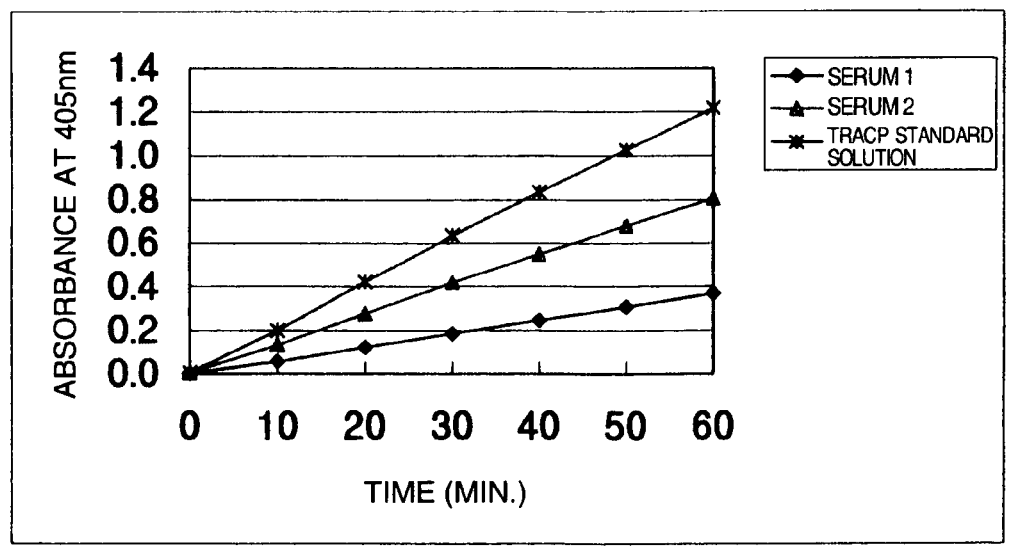
FIG. 2 is a graph obtained by treating a specimen (a standard solution or serum) with a plate having an antibody against TRACP 5b immobilized thereon, and then assaying the enzymatic activity by a rate method by using 2-chloro-4-nitrophenylphosphoric acid as a substrate for enzyme.

To each well of a plate having an anti-TRACP 5b antibody TrK27 immobilized thereon was applied 100 µl of a specimen (a standard solution or serum), and stirred with shaking at room temperature for 1 hour. Then, the reaction solution was discarded and each well was washed three times with 200 µL of Tris buffer containing 0.05% Tween 20. Thereafter, 100 µl of a buffer solution containing a substrate (CNPP) was added to each well and shaken for 30 seconds, and then absorbance at 405 nm was measured with a microtiter plate reader. Subsequently, the plate was heated in an incubator at 37° C. for 60 minutes. During the incubation, absorbance at 405 nm was measured at intervals of 10 minutes. On the other hand, the following method was adopted as a comparative method (an end-point method): 60 minutes after the start of the incubation, 50 µl of 0.2N NaOH was added to each well as a reaction-terminating solution and absorbance at 405 nm was similarly measured. FIG. 2 shows the reaction time course studied over a period of 60 minutes. The TRACP 5b activity level is calculated by the following equation:

U/L=ΔOD/min of specimen/ΔOD/min of standard solution×activity value of standard solution wherein ΔOD/min is an absorbance change per minute at a measuring wavelength of 405 nm.

A rate method was practiced by measuring an absorbance change per minute during a period between 10 minutes and 20 minutes after the start of the incubation, and calculating the activity by the above equation. As a result, the TRACP 5b activity levels of serum specimens 1 and 2 were found to be 4.1 U/L and 9.1 U/L. These levels were substantially the same as 4.2 U/L and 9.3 U/L which were levels measured after the addition of the reaction-terminating solution after 60 minutes of the reaction in the end-point method. Therefore, it has been proved that the present invention makes it possible to assay TRACP 5b activity in about 20 minutes by the rate method without using a terminating solution.

INDUSTRIAL APPLICABILITY

As explained above in detail, the immunoassay method of the present invention makes it possible to assay TRACP 5b in a specimen specifically with high sensitivity with almost no influence of TRACP 5a in the specimen. Therefore, TRACP 5b can be more accurately assayed than before.

The invention claimed is:

1. An immunoassay method for determining tartrate resistant acid phosphatase 5b (TRACP 5b) in a specimen, the method comprises binding both TRACP 5b and TRACP 5a in the specimen to an antibody that is reactive with both of TRACP 5b and TRACP 5a, separating the TRACP 5a and TRACP 5b bound to the antibody, and subjecting the TRACP 5a and TRACP 5b bound to the antibody to enzyme reaction with a 2-halo-4-nitrophenylphosphoric acid represented by the general formula (1):

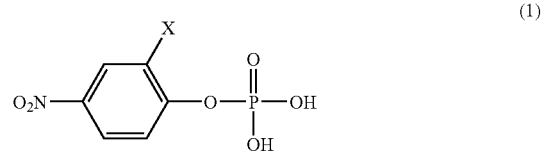

(1)

wherein X is Cl, or a salt of the compound of general formula (I), which is a substrate more specific for TRACP 5b than for TRACP 5a, and then assaying the enzymatic activity of said enzyme reaction to determine TRACP 5b to carry out the immunoassay of TRACP 5b in the specimen, wherein at the time of the enzyme reaction, the pH is higher than 6.3 and not higher than 6.8.

2. An immunoassay method according to claim 1, wherein at the time of the enzyme reaction, the pH is 6.35 to 6.75.

3. An immunoassay method according to claim 2, wherein the assay of the enzymatic activity is carried out by an end-point method.

4. An immunoassay method according to claim 1, wherein the assay of the enzymatic activity is carried out by an end-point method.

* * * * *